United States Patent
Nanni

(10) Patent No.: US 6,755,652 B2
(45) Date of Patent: Jun. 29, 2004

(54) METHOD FOR PRODUCING DENTAL RESTORATION ELEMENTS

(75) Inventor: Marco Nanni, Meran (IT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 10/253,081

(22) Filed: Sep. 23, 2002

(65) Prior Publication Data

US 2003/0157461 A1 Aug. 21, 2003

Related U.S. Application Data

(60) Provisional application No. 60/364,802, filed on Mar. 17, 2002.

(30) Foreign Application Priority Data

Feb. 15, 2002 (DE) .......................................... 102 06 429

(51) Int. Cl.[7] .............................................. A61C 13/10
(52) U.S. Cl. ......................................... 433/196; 433/75
(58) Field of Search ........................... 433/196, 72, 75, 433/76, 67, 213, 173; 606/96, 97; 33/513

(56) References Cited

U.S. PATENT DOCUMENTS 4,629,746 A * 12/1986 Michl et al. ................. 523/117
5,320,529 A * 6/1994 Pompa ......................... 433/76
5,415,546 A * 5/1995 Cox, Sr. ...................... 433/213
5,636,986 A * 6/1997 Pezeshkian ................... 433/76
5,915,962 A * 6/1999 Rosenlicht .................... 433/76

FOREIGN PATENT DOCUMENTS

DE          3621952 A1     1/1988

* cited by examiner

*Primary Examiner*—Kevin Shaver
*Assistant Examiner*—Melba Bumgarner
(74) *Attorney, Agent, or Firm*—John C. Thompson; Alan S. Korman

(57) ABSTRACT

A method for preparing dental restoration which is to be secured in the mouth of a dental patient includes providing a base plate with ready made x-ray opaque restorative teeth thereon, the base plate being formed in correspondence with the mouth of the patient in which the restorative teeth are to be fixedly secured. The base plate is temporarily situated in the patient's mouth and then the temporarily situated position of the base plate in the patient's mouth is observed, preferably via an x-ray. The temporarily situated position of the base plate in the patient's mouth is assessed to determine predetermined locations at which drill holes for facilitating the fixed securement of the restorative teeth in the patient's mouth are to be bored.

5 Claims, 1 Drawing Sheet

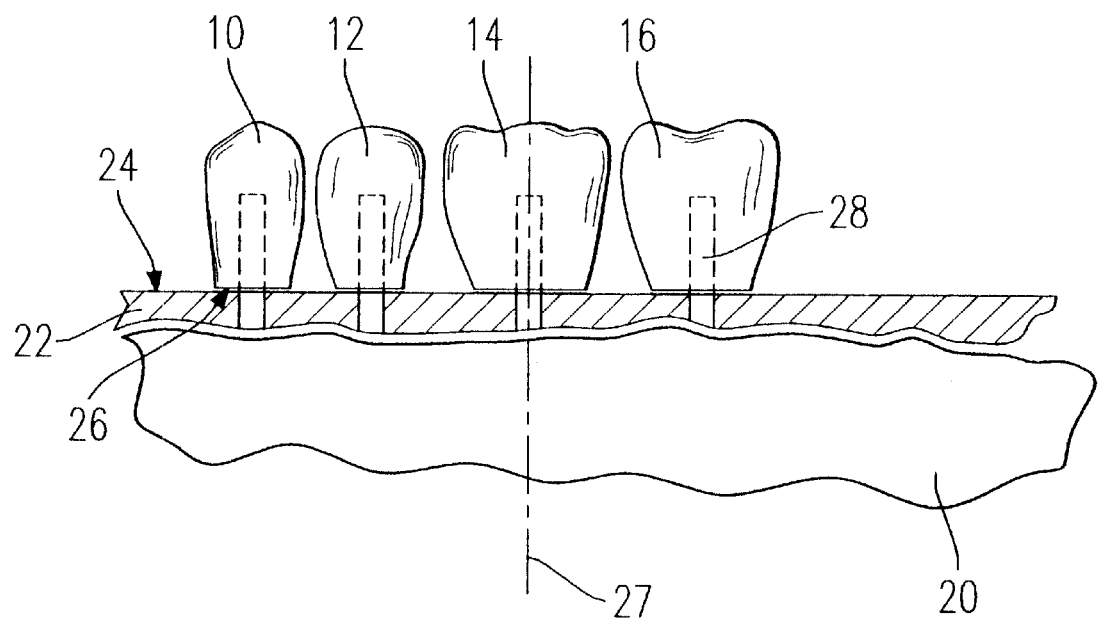

US 6,755,652 B2

METHOD FOR PRODUCING DENTAL RESTORATION ELEMENTS

CROSS-REFERENCE TO RELATED APPLICATIONS

This application claims foreign priority benefits under 35 U.S.C. §119(a)–(d) from German patent application ser. no. P 102 06 429.6 filed Feb. 15, 2002. In addition, this application claims the benefit under 35 U.S.C. §119(e) of U.S. provisional patent application Ser. No. 60/364,802 filed Mar. 17, 2002.

BACKGROUND OF THE INVENTION

The present invention relates to a method for producing dental restoration elements.

A method for producing dental restoration elements has long been known, as shown, for example, in DE-OS 36 21 952, which shows a practice model for simulating the placement of dental restoration elements.

It is further conventionally known to use so-called drill guides as an aid for planning the location or disposition of implants which will ultimately be placed in the patient's mouth. With regard to the anchoring of the implants in the jaw mass, it is critical that sufficient jaw mass is available. In this connection, drill holes for the anchoring or fastening of the implants must be created at the proper locations on the jaw.

On the other hand, each displacement or shifting of a drill hole axis results in a displacement of the position of the implant, so that the impact of such a displacement on the upper and lower teeth alignment must be assessed. Sometimes, the decision on where to locate the drill holes which will receive the implants must be further revised if it transpires that, at a particular location, too little jaw mass is available, in which event the location of the drill hole must be changed. As the dentist or the dental technician has heretofore himself or herself prepared the teeth to be secured in the patient's mouth, it is possible, in such an event, to undertake a modification or a revision in order to improve the jaw and teeth alignment situation.

In connection with performing, via an x-ray confirmation, a quality control of the installation of a dental restoration element, the dental technician mixes into the polymerizable material mixture of the dental restoration element a contrast medium for the x-rays, whereby the position of the dental structure is visible in an x-ray of the patient's mouth. By the use of a drill guide process, it is ensured that the dentist, by examining such an x-ray, can plan or forecast the position of the dental restoration element in the mouth of the patient before fixing the locations of the drill holes in the jaw.

This method requires, however, a substantial effort and requires that the work be undertaken with great precision in order to avoid the occurrence of misalignments during the establishment of the drill axes. The drill guide most typically includes a top surface on which the freshly prepared, x-ray opaque teeth structures can be secured by adhesion. If the individually formed teeth are not then placed by the dental technician very precisely at the proper angle, there occurs an angle misalignment, in that the teeth, which are subsequently secured via adhesive securement to the base plate, are secured such that the drill axes are oriented with a corresponding angle misalignment. The dentist can, to be sure, rectify or improve this situation in that the dentist can place the drill axes somewhat at an angle or inclination. This, however, requires considerable skill and experience, which are likewise demanded in connection with the production of dental teeth by hand, whereby, at most, only a dental-like, non-exact structure is produced.

SUMMARY OF THE INVENTION

The present invention offers a solution to the challenge of providing a method for producing dental restoration elements having implants, which, at the same time, permits cost savings to be realized and the precision of the dental restoration element installation process to be increased.

The method of the present invention permits surprisingly simple substances to be used to optimize the position of implants. By the use of industrial pre-prepared teeth which are, at the same time, x-ray opaque, the necessity to perform follow-on or revision work is substantially reduced. The precision and reproducibility are substantially greater than is found in connection with teeth which are individually formed by a dental technician, so that, from the inception of the process onward, the teeth can be placed in a functional manner in the mouth of the patient. Also, the undersides of the industrially prepared teeth have true angles and are planar so that misalignment or out-of-alignment tipping is effectively foreclosed. The necessity to displace the teeth after their disposition in the mouth of the patient in order to compensate for angle misalignment is, in this regard, clearly reduced. The drill guide can serve, in accordance with the method of the present invention, in a conventional role as a guide for the drill holes so that the dentist is in the position to form the drill holes in the jawbone and accommodate the dental restoration elements to the particular configuration of the patient's mouth.

It is particularly advantageous that the configurations and fixed securement of industrially produced teeth are better than those teeth individually formed by a dental technician through a mixing and finishing process. In this connection, closely adjacent drill holes can be realized as well without creating the danger that the teeth will break. An additional perspective is that the exact contour of the tooth as shown in the x-ray can be achieved by the use of industrially pre-prepared teeth. Due to the improved production of such teeth, a greater portion of an x-ray contrast substance such as, for example, barium sulfate, can be used, whereby the contour of the teeth is substantially more visible.

Further advantages, details, and features are set forth in the hereinafter following description of an embodiment of the method of the present invention.

BRIEF DESCRIPTION OF THE DRAWINGS

The sole FIGURE of the drawing is a sectional elevational view of a drill guide having thereon teeth formed in accordance with the present invention, the drill guide and the thereon secured teeth being disposed on a tooth-free jaw.

DETAILED DESCRIPTION OF THE PREFERRED EMBODIMENT

In accordance with the present invention, pre-prepared x-ray opaque teeth, of which four teeth, 10, 12, 14 and 16 are shown in the sole figure of the drawing, are used for the realization of the dental restoration element. In accordance with the present invention, in an initial step, an impression is taken in a conventional manner of the patient's mouth and a model is then formed of the patient's mouth based upon the impression. In the example illustrated herein, a jaw 20 having no teeth thereon is illustrated, whereby it is to be understood that, as well, partial prosthetics can be used in accordance with the method of the present invention. The dental technician prepares, in accordance with the configuration of the patient's mouth, a base plate with teeth—the so-called drill guide 22. In the illustrated embodiment, the drill guide is completed after the jaw impression has been taken and correspondingly exhibits, along its underside, a contour which corresponds to that of the top surface of the jaw.

The drill guide includes a top surface 24. In accordance with the current invention, the industrially pre-prepared (ready made) and x-ray opaque teeth 10–16 are secured to the top surface 24 via adhesion, via polymerization, or in any other suitable manner. In this connection, a conventional, commercially available adhesive means can be used which exhibits sufficient adhesive strength to permit drilling through the drill guide 22, with the thereon secured teeth, without the teeth being loosened, but which also permits, on the other hand, removal of the teeth from the drill guide; this being accomplished, for example, by securement of the teeth to the drill guide by counter boring or counter sinking. The industrially pre-prepared teeth exhibit a high compositional integrity.

Once the teeth have been disposed on the drill guide to the satisfaction of the dentist, the dentist then sets the drill guide 22 together with the teeth 10–16 thereon in the mouth of the patient and takes at least one x-ray of the set up. The x-ray or x-rays permit the position of the teeth to be determined with respect to the jaw and it can be determined in which manner the drill holes are to be bored through the teeth 10–16—and thereby, as well as, the manner in which the drill holes in the jaw 20 should be undertaken. In this connection, a drill axis 27 is shown in the tooth 14. The dentist or, respectively, the dental technician, thereafter prepares the corresponding drill holes, whereby—as can be seen in the sole figure of the drawing, the drill guide 22 as well as the respective tooth 16 are drilled through to form a drill hole 28.

In view of the fact that the precision of the placement of the teeth is improved by the method of the present invention, a drill guide 22 having a markedly small thickness can be deployed as well. The teeth 10–16 are, for example, not removed and the dentist drills through the teeth and the drill guide 22 to the corresponding drill holes in the jaw 20 of the patient. The dentist can alternatively use the drill guide to establish the location of the holes to be drilled in the jaw by marking the planned drill holes on the jaw as indicated by the holes formed in the drill guide. In this connection, the dentist marks the holes by, for example, a pen point, on the jawbone. Thereafter, the drill guide is removed and the drill holes are drilled directly into the jawbone. In a conventionally known manner, the dentist threads the implants into the holes formed in the jawbone and the dental restoration elements are then disposed in a conventional manner onto the implants. Due to the good adhesive securement properties of the industrial pre-prepared teeth, this technology also makes it possible to handle small teeth as well, including the teeth in the front jaw region.

The securement can follow in a conventional manner as well via an abutment. Additionally, the realization of the x-ray opaqueness of the inventive teeth 10–16 is not limited to the use of barium sulfate but, instead, can also be undertaken with any suitable x-ray contrast substance. For example, a suitable x-ray contrast substance can be a metallic powder or preferably ytterbium tri-fluoride.

The specification incorporates by reference the disclosure of German priority document 102 06 429.6.

The present invention is, of course, in no way restricted to the specific disclosure of the specification and drawings, but also encompasses any modifications within the scope of the appended claims.

What is claimed is:

1. A method for preparing dental restoration which is to be secured in the mouth of a dental patient, comprising:

making a base plate by taking an impression in the mouth of patient, the base plate having a generally planar top surface;

adhesively securing restorative teeth onto the generally planar top surface of base plate, the undersides of the restorative teeth being planar so that misalignment when they are placed on the surface;

temporarily situating the base place with the restorative teeth thereon in the patient's mouth;

observing the temporarily situated position of the base plate in the patient's mouth via a selected one of an x-ray assisted observation or a non x-ray assisted observation;

assessing the temporarily situated position of the base plate in the patient's mouth to determine predetermined locations at which drill holes are to be bored, the drill holes serving for facilitating the fixed securement of the restorative teeth in the patient's mouth; and boring the drill holes at the predetermined drill hole locations in the base plate and the restorative teeth.

2. A method according to claim 1, wherein the temporarily situated position of the base plate in the patient's mouth is observed via an x-ray assisted observation which includes an x-ray of the temporarily situated base plate, with the restorative teeth secured thereon, in the patient's mouth.

3. A method according to claim 1 and further comprising removing the restorative teeth from the base plate after the base plate has been taken out of the patient's mouth, the drill holes in the base plate indicating drill hole locations for subsequent installation of implants in the patient's mouth.

4. A method according to claim 1 and further comprising preparing dental restoration based upon the restorative teeth and securing the dental restoration to an implant in the patient's mouth via a selected one of an abutment and a non-abutment anchoring means.

5. A method according to claim 1, wherein the restorative teeth comprise an x-ray opaque material.

* * * * *

UNITED STATES PATENT AND TRADEMARK OFFICE
CERTIFICATE OF CORRECTION

PATENT NO. : 6,755,652 B2
DATED : June 29, 2004
INVENTOR(S) : Marco Nanni

It is certified that error appears in the above-identified patent and that said Letters Patent is hereby corrected as shown below:

<u>Column 4,</u>
Line 7, insert -- the -- after "surface of";
Line 8, insert at the end of the line -- or out f alignment tipping of the restorative teeth is effectively foreclosed --.

Signed and Sealed this

Twenty-fourth Day of August, 2004

JON W. DUDAS
*Director of the United States Patent and Trademark Office*